(12) United States Patent
Baum et al.

(10) Patent No.: US 8,287,631 B2
(45) Date of Patent: Oct. 16, 2012

(54) COMPOUNDS FOR PREVENTING GHOST ODOUR

(75) Inventors: Rudiger Baum, Waghusel (DE);
Hans-Jurgen Schmidt, Speyer (DE);
Thomas Wunder, Neustadt (DE);
Christos Savides, Fairfield, CT (US)

(73) Assignee: THOR GmbH, Speyer (DE)

( * ) Notice: Subject to any disclaimer, the term of this patent is extended or adjusted under 35 U.S.C. 154(b) by 0 days.

(21) Appl. No.: 12/657,861

(22) Filed: Jan. 28, 2010

(65) Prior Publication Data
US 2010/0186631 A1 Jul. 29, 2010

(30) Foreign Application Priority Data

Jan. 29, 2009 (EP) ..................................... 09151677

(51) Int. Cl.
*C09D 5/14* (2006.01)
*C09D 5/02* (2006.01)
*A01N 25/00* (2006.01)
*A01N 43/80* (2006.01)
*A01P 1/00* (2006.01)
*A01P 3/00* (2006.01)

(52) U.S. Cl. ............... 106/18.33; 106/15.05; 106/18.32; 106/18.34; 106/18.35; 424/78.09; 424/406; 514/360; 524/83

(58) Field of Classification Search ............... 106/15.05, 106/18.32, 18.34, 18.35, 18.33; 424/78.09, 424/406; 514/360; 524/83
See application file for complete search history.

(56) References Cited

U.S. PATENT DOCUMENTS

| 3,615,745 | A | 10/1971 | Kenney | |
|---|---|---|---|---|
| 6,566,382 | B2 * | 5/2003 | Still et al. | 514/372 |
| 7,767,729 | B2 * | 8/2010 | Ashmore et al. | 523/102 |
| 2009/0203643 | A1 * | 8/2009 | Patel | 514/55 |

FOREIGN PATENT DOCUMENTS

| EP | 1 961 792 A1 | | 8/2008 |
|---|---|---|---|
| JP | 2003-226846 A | * | 8/2003 |
| JP | 2005-154965 A | * | 6/2005 |
| JP | 2005-270214 A | * | 10/2005 |
| JP | 2005-298494 A | * | 10/2005 |
| WO | WO2005/021626 A2 | * | 3/2005 |
| WO | WO2006/042128 A2 | | 4/2006 |
| WO | 2007/092632 A2 | * | 8/2007 |
| WO | WO2008148855 A1 | | 12/2008 |

* cited by examiner

*Primary Examiner* — Anthony J Green

(74) *Attorney, Agent, or Firm* — Hedman & Costigan, P.C.; James V. Costigan

(57) ABSTRACT

The invention relates to compounds from the groups of (A) electrophiles, (B) nucleophiles, (C) alkylating agents, (D) antioxidants and (E) oxidizing agents as odor preventatives for reducing so-called ghost odor which is induced by 2-methyl-4-isothiazolin-3-one and/or octyl-4-isothiazolin-3-one. The invention further relates to biocide compositions which comprise 2-methyl-4-isothiazolin-3-one and/or octyl-4-isothiazolin-3-one and also one or more odor preventatives, and to the use of odor preventatives for preventing ghost odor.

4 Claims, No Drawings

COMPOUNDS FOR PREVENTING GHOST ODOUR

The invention relates to the use of compounds from the groups of (A) electrophiles, (B) nucleophiles, (C) alkylating agents, (D) antioxidants and (E) oxidizing agents as odour preventatives for reducing so-called ghost odour in coating compositions and coatings which is induced by 2-methyl-4-isothiazolin-3-one and/or octyl-4-isothiazolin-3-one. The invention further relates to biocide compositions which comprise 2-methyl-4-isothiazolin-3-one and/or octyl-4-isothiazolin-3-one and also one or more odour preventatives.

When surfaces are coated with coating compositions such as emulsion paints there are frequently unpleasant odours. These odours are perceived as being particularly unpleasant especially in the interior sector, owing to inadequate ventilation.

Frequently such odours can be attributed to volatile ingredients of the coating composition (VOCs; volatile organic compounds) which have an intense intrinsic odour. The VOCs are, for example, solvents, amines or residual monomers from the binder. Nuisance odours attributable to VOC constituents are in general of limited duration and no longer occur as soon as volatile ingredients have evaporated completely from the coating.

The incidence of nuisance odours may also be induced by microbial infestation (MVOC; microbial VOC) of the coating. This microbial infestation may be induced by the coating composition itself, by the coating substrate or by interaction of the coating composition with the coating substrate. Microbial infestation due to external factors is also possible, such as moulding on damp walls as a consequence of high atmospheric humidity or inadequate ventilation, or as a result of structural deficiencies and the like.

The incidence of this kind of nuisance odour is known, and the prior art has disclosed diverse solutions for preventing or reducing such nuisance odours. Thus there are numerous VOC-free coating compositions known that can be used to prevent VOC-related nuisance odours.

The incidence of nuisance odours attributable to MVOC can be reduced or prevented by effective preservation of the coating composition itself and also by appropriate treatment of the coating substrate and the elimination of external factors.

A hitherto largely unresearched and to date unresolved problem is that referred to as "ghost odour". It entails a nuisance odour occurring in rooms that have coatings that have already dried and filmed, and in some cases coatings that are already fairly old. This ghost odour may occur days, weeks or months after the coating has been applied, and is described and perceived as being like cat's urine, perspiration, onion, rubber or fruit. It is also known that this ghost odour can be perceived with particular intensity in warm weather and at relatively high atmospheric humidity, in many cases even after a room has been ventilated, under intense sunlight, and especially in association with exposure to ozone.

Investigations show that sulphur compounds are critically involved in the development of the odour. Sulphur compounds in coating compositions may originate from many different sources. They may be present in the products themselves or in the raw materials used to prepare them, as part of the formula, or may be present as contaminants that are due to production, storage or transport. The sulphur compounds in question may be compounds either of synthetic origin or of biogenic origin. Compounds which may give rise to the incidence of ghost odour in coatings or coating composition are 2-methyl-4-isothiazolin-3-one and octyl-4-isothiazolin-3-one.

The method described in the examples allows standardized detection of the ghost odour. Persons with a normal sense of smell who have been exposed to the ghost odour are able to recognize this odour again beyond doubt.

Avoiding sulphur compounds in coating materials in order to prevent ghost odour is often difficult, since extremely small amounts may give rise to the odour.

It is an object of the invention to provide compounds for the at least extensive prevention or reduction of ghost odour in coatings, containers and biocide compositions comprising 2-methyl-4-isothiazolin-3-one and/or octyl-4-isothiazolin-3-one. It is a further object of the invention to provide biocide compositions which comprise 2-methyl-4-isothiazolin-3-one and/or octyl-4-isothiazolin-3-one and feature reduced incidence of ghost odour.

This object is achieved by the use of one or more of the compounds recited below from one or more of the below-defined groups of (A) electrophiles, (B) nucleophiles, (C) alkylating agents, (E) antioxidants and (E) oxidizing agents for preventing or reducing ghost odour in coating compositions and coatings which comprise 2-methyl-4-isothiazolin-3-one (MIT below) and/or octyl-4-isothiazolin-3-one (OIT below).

These compounds are suitable for at least extensively reducing the incidence of ghost odour in coating compositions, containers and coatings which comprise MIT and/or OIT. These coating compositions may be selected from industrial products and materials such as paints, varnishes, stains and renders, emulsions, lattices and polymer dispersions. The compounds are additionally suitable for at least extensive prevention or at least extensive reduction of ghost odour in chalk suspensions, mineral slurries, adhesives, pigment pastes and pigment dispersions, thickeners, liquids and raw materials in paper processing. With preference the compounds of the invention are suitable for preventing ghost odour in coatings which are obtainable by application of the aforementioned coating compositions to surfaces (a drying step may be necessary). The compounds are suitable, furthermore, for the prevention of ghost odour in the corresponding containers comprising MIT and/or OIT as preservatives. By "container" is meant the above-recited coating compositions in storage in a vessel such as a tank or pail. Where concentration figures are given below that relate to a container, those figures likewise apply to the corresponding coating compositions.

The inventive use of one or more of the compounds recited below from groups (A) to (E) is particularly appropriate to coating compositions from the group of emulsion paints and also their starting materials, especially polymer dispersions.

The use of the inhibitors of the invention from groups (A) to (E) is additionally suitable in wall-paints, especially in water-based wall-paints for the coating of interior surfaces.

In a further preferred embodiment of the invention the inhibitors are used for preventing ghost odour in containers or coatings and coatings which are preserved with an MIT/BIT mixture, an MIT/OIT mixture, an MIT/bronopol mixture, MIT/pyrithione mixture, especially MIT/zinc pyrithione and MIT/sodium pyrithione, an MIT/DCOIT mixture, MIT/CMIT mixture, an MIT/CMIT/BIT mixture, an MIT/dithio-bisbenzmethylamide mixture, an MIT/quat mixture, especially MIT/benzalkonium chloride and MIT/dimethyldidecylammonium chloride, an MIT/biguanidine mixture, especially MIT/polyhexamethylenebiguanide, an MIT/DBNPA mixture, an MIT/formaldehyde donor mixture, especially MIT/tetramethylolacetylenediurea, an MIT/N-alkyl-BIT mixture, especially MIT/N-methyl-BIT and MIT/N-butyl-BIT, an MIT/IPBC mixture, an MIT/o-phenylphenol mixture, an MIT/IPBC mixture, an MIT/Ag mixture, an OIT/Ag mixture, OIT/formaldehyde donor mixture, especially OIT/tetramethylolacetylenediurea, an OIT/glutaraldehyde mixture, an OIT/IPBC mixture, an OIT/pyrithione mixture, especially OIT/zinc pyrithione and OIT/sodium pyrithione, an OIT/carbendazim mixture, OIT/BIT mixture, OIT/MIT/CMIT mixture, with an OIT/dithiobisbenzmethylamide mixture, with an OIT/N-alkyl-BIT mixture, especially OIT/N-methyl-BIT and OIT/N-butyl-BIT, an OIT/quat mixture, especially OIT/benzalkonium chloride and OIT/dimethyldidecylammonium chloride.

The application concentrations of the above-stated biocide mixtures are typically in the range from 1 to 2000 ppm, preferably in the range from 1 to 1000 ppm and with more particular preference in the range from 1 to 500 ppm, based on their concentration in the container. For all of the applications the concentrations of the inhibitors are typically in the range from 1 to 1000 ppm, preferably in the range from 1 to 100 ppm and with more particular preference in the range from 1 to 10 ppm, based on their concentration in the container.

In one embodiment of the invention the inhibitors are biocides. In an alternative embodiment of the invention the inhibitors are not biocides, i.e., they either possess no biocidal action at all or else in the application are present in a concentration at which they do not develop a biocidal action. In that case they serve only to reduce the incidence of ghost odour and do not make any detectable contribution to the preservation.

In general the ratio of preservative or biocide to inhibitor is in the range from 1000:1 to 1:100, preferred ratios are in the range from 100:1 to 1:10, with ratios in the range from 10:1 to 1:1 being more particularly preferred.

Suitable compounds from the group of electrophiles (A) are $C_1$ to $C_6$ mono- and dialdehydes, with the exception of the compounds formaldehyde, glyoxal and glutaraldehyde. Additionally suitable compounds are acetaldehyde, unsaturated $C_1$ to $C_6$ mono- and dialdehydes such as succinaldehyde, acrolein, α-bromocinnamaldehyde (BCA). Further suitable compounds from the group of electrophiles (A) are formaldehyde donors, also called formaldehyde depot substances. Formaldehyde-depot substances are compounds which give off formaldehyde in a chemical reaction. Compounds of this kind are specified and defined in, for example, the standard reference work in the microbicide field, Wilfried Paulus: *Directory of Microbicides for the Protection of Materials and Processes*. Springer Netherlands, Berlin 2006, ISBN 1-402-04861-0 in the chapter "Formaldehyde Releasing Compounds". Important in the formaldehyde depot substances is the presence of certain functional groups, such as a hydroxymethyl group, for example. Examples of formaldehyde depot substances are compounds such as n-butanol hemiformal, benzalkonium hemiformal, 2-phenoxyethanol hemiformal, ethylene glycol hemiformal, 3-iodopropargyl (4-chlorophenyl) formal, tetra(hydroxymethyl)phosphonium sulphate (THPS), 2-hydroxy-2-nitropropane-1,3-diol, di(hydroxymethyl)uron, hemiacetals, dimethylolurea, tetrahydroxymethylacetylenediurea, 1,6-dihydroxyl-2,5-dioxahexane, reaction products of amines with formaldehyde, especially hexamine derivatives such as hexamine, N-(3-chloroallyl)hexaminium chloride, 1,3-oxazolidines, 1,3-oxazines, 1,3,5-substituted hexahydrotriazines (HHT), diaminomethane derivatives such as dimorpholinomethane, reaction products of amides and formaldehyde, such as N-hydroxymethylamides such as N-methylolchloroacetamide, 2,2,3-trichloro-N-hydroxymethylpropionamide, N-hydroxymethylureas, diazolidinylureas, imidazolidinylureas, methyloldimethylhydantoins, reaction products of amino acids and formaldehyde such as sodium hydroxymethylglycinates and tauroline.

Further electrophiles are suitably activated compounds such as thiocyanates or isothiocyanates, such as methylene bisthiocyanate, iodomethyl thiocyanate, allyl isothiocyanate.

Suitability is further possessed by:
  carboxamides such as 2-chloroacetamide, 2-bromoacetamide, 2-iodoacetamide, N-(4-bromo-2-methylphenyl)-2-chloroacetamide (BMPCA), 2,2-dibromo-3-nitrilopropionamide (DBNPA), 2,2-dibromo-2-nitroacetamide, N-hydroxymethylchloroacetamide
  C-methylols such as, for example, 2-bromo-2-nitropropan-1-ol (BNP), 2-bromo-2-nitropropan-1-ol, 5-bromo-5-nitro-1,3-dioxane
  reaction products of amides and formaldehyde, e.g. N-hydroxymethylamides such as N-methylolchloroacetamide or 2,2,3-trichloro-N-hydroxymethylpropionamide
  α-halo carboxylic acids such as chloroacetic, bromoacetic and iodoacetic acid, α-halo carboxylic esters such as ethyl bromoacetate, benzyl bromoacetate, 1-bromo-3-ethoxycarbonyloxy-1,2-diiodo-1-propene, 1,4-bis(bromoacetoxy)-2-butene (BBAB), 1,2-bis(bromoacetoxy)ethane, 2-bromo-4'-hydroxyacetophenone, 2,3-dibromo (2-hydroxy)ethylpropionate
  halomethyl-sulphonic acid derivatives (halogen=Cl, Br, I) such as bis(trichloro-methyl) sulphone, p-[(diiodomethyl)sulphonyl]toluene, p-[(iodomethyl)sulphonyl] toluene, p-[(dibromomethyl)sulphonyl]toluene, p-[(bromomethyl)sulphonyl]toluene, p-[(diiodomethyl)sulphonyl]pyridine, p-[(diiodomethyl)sulphonyl]pyridine 1-oxide, p-[(iodomethyl)sulphonyl]pyridine, p-[(iodomethyl)sulphonyl]pyridine 1-oxide, p-[(dibromomethyl)sulphonyl]pyridine, p-[(dibromomethyl)sulphonyl]pyridine 1-oxide, p-[(bromo-methyl)sulphonyl]pyridine, p-[(bromomethyl)sulphonyl]pyridine 1-oxide, (2-chloro-2-cyanovinyl phenyl sulphone, 3,3,4,4-tetrachlorotetrahydro-1,1-dioxothiophene, [(tribromomethypsulphonyl]benzene, [(bromonitromethyl)sulphonyl] benzene, [(dibromonitromethyl)sulphonyl]benzene, [[(dibromomethyl)sulphonyl]methyl]benzene, 2-iodo-1-propenyl phenyl sulphone, (2-chloro-1-hexenyl)phenyl sulphone.

Further suitable electrophiles are compounds according to the general structural formula I,

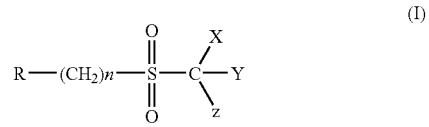

where
R is selected from the group consisting of H, alkyl, cycloalkyl, aralkyl, aryl, alkoxyaryl and heteroaryl, the groups alkyl, cycloalkyl, aralkyl, aryl, alkoxyaryl and heteroaryl being optionally substituted by one or more substituents.

The substituents are selected independently of each other from the group consisting of fluorine, chlorine, bromine, iodine, hydroxyl, unsubstituted or substituted alkyl, unsubstituted or substituted aryl, unsubstituted or substituted heteroaryl, unsubstituted or substituted aralkyl, alkoxy, amino, nitro, carboxyl, carboalkoxy, cyano, alkylamino, hydroxyalkyl, mercaptyl, alkylmercaptyl, trihaloalkyl, carboxyalkyl, carbamoyl, —($C_1$-$C_7$)alkyl, —$PF_3$, —O—($C_1$-$C_7$)alkyl, —NH—($C_1$-$C_4$)alkyl, —N(($C_1$-$C_4$)alkyl)$_2$, —NH—CHO, —NH—CO—($C_1$-$C_4$)alkyl, —CO—$NH_2$, —CO—NH—($C_1$-$C_4$)alkyl, —CO—N(($C_1$-$C_4$)alkyl)$_2$ and —CO—OH.

X, Y and Z are selected independently of one another from the group consisting of hydrogen, fluorine, chlorine, bromine and iodine, with at least one of X, Y and Z being a halogen atom. In a further preferred embodiment of the invention X, Y and Z are selected independently of one another from the group consisting of hydrogen, fluorine, chlorine, bromine and iodine, with at least two being a halogen atom. In a particularly preferred embodiment of the invention X, Y and Z are selected independently of one another from the group consisting of hydrogen, fluorine, chlorine, bromine and iodine, and have a total atomic weight of more than 110.

n is an integer from 0 to 4. In one preferred embodiment of the invention n is an integer from 0 to 2, and more preferably n is 0.

"Alkyl" denotes a saturated aliphatic hydrocarbon group, which may be straight-chain or branched and may have from 1 to 20 carbon atoms in the chain. Preferred alkyl groups may be straight-chain or branched and have from 1 up to 10 carbon atoms in the chain. Branched means that a lower alkyl group, such as methyl, ethyl or propyl, is attached to a linear alkyl chain. Alkyl is for example methyl, ethyl, 1-propyl, 2-propyl, 1-butyl, 2-butyl, 2-methyl-1-propyl(isobutyl), 2-methyl-2-propyl(tert-butyl), 1-pentyl, 2-pentyl, 3-pentyl, 2-methyl-1-butyl, 3-methyl-1-butyl, 2-methyl-2-butyl, 3-methyl-2-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,2-dimethyl-1-butyl, 2,3-dimethyl-1-butyl, 3,3-dimethyl-1-butyl, 2-ethyl-1-butyl, 2,3-dimethyl-2-butyl, 3,3-dimethyl-2-butyl, 1-heptyl, 1-octyl, 1-nonyl, 1-decyl, 1-undecyl, 1-dodecyl, 1-tetradecyl, 1-hexadecyl and 1-octadecyl. "Substituted alkyl" means that the alkyl group is substituted by one or more substituents selected from alkyl, unsubstituted or substituted aryl, unsubstituted or substituted aralkyl, alkoxy, amino, nitro, carboxyl, carboalkoxy, cyano, alkylamino, halo, hydroxyl, hydroxyalkyl, mercaptyl, alkylmercaptyl, trihaloalkyl, carboxyalkyl or carbamoyl.

"Cycloalkyl" denotes an aliphatic ring which has from 3 to approximately 10 carbon atoms in the ring. Preferred cycloalkyl groups have from 4 to approximately 7 carbon atoms in the ring.

"Aralkyl" denotes an alkyl group which is substituted by an aryl radical, with "aryl" denoting phenyl or naphthyl. "Substituted aralkyl" and "substituted aryl" mean that the aryl group, or the aryl group of the aralkyl group, is substituted by one or more substituents selected from alkyl, alkoxy, amino, nitro, carboxyl, carboalkoxy, cyano, alkylamino, halo, hydroxyl, hydroxyalkyl, mercaptyl, alkylmercaptyl, trihaloalkyl, carboxyalkyl or carbamoyl.

"Alkoxy" denotes an alkyl-O— group in which "alkyl" has the definition described above. Lower alkoxy groups are preferred. Included as exemplary groups are methoxy, ethoxy, n-propoxy, isopropoxy and n-butoxy.

"Lower alkyl" denotes an alkyl group containing 1 to approximately 7 carbon atoms.

"Alkoxyalkyl" denotes an alkyl group as described above which is substituted with an alkoxy group as described above.

"Halogen" (or "halo") denotes chlorine (chloro), fluorine (fluoro), bromine (bromo) or iodine (iodo).

"Heterocyclyl" denotes an approximately 4- to approximately 10-membered ring structure in which one or more of the ring atoms is an element other than carbon, such as N, O or S, for example. Heterocyclyl may be aromatic or non-aromatic; i.e. it may be saturated, partially unsaturated or wholly unsaturated.

Preferred heterocyclyl groups included are as follows: pyridyl, pyridazinyl, pyrimidinyl, isoquinolyl, quinolyl, quinazolinyl, imidazolyl, pyrrolyl, furanyl, thienyl, thiazolyl, benzothiazolyl, piperidyl, pyrrolidinyl, tetrahydrofuranyl, tetrahydropyranyl and morpholinyl groups.

"Substituted heterocyclyl" means that the heterocyclyl group is substituted by one or more substituents, substituents included being as follows: alkoxy, alkylamino, aryl, carbalkoxy, carbamoyl, cyano, halo, heterocyclyl, trihalomethyl, hydroxyl, mercaptyl, alkylmercaptyl or nitro.

"Hydroxyalkyl" denotes an alkyl group which is substituted by a hydroxyl group. Hydroxy-lower alkyl groups are preferred. Exemplarily preferred groups included are as follows: hydroxymethyl, 2-hydroxyethyl, 2-hydroxypropyl and 3-hydroxypropyl.

"Carboxyl" denotes a COOH group.

"Alkoxycarbonyl" denotes an alkoxy-C=O group.

"Aralkoxycarbonyl" denotes an aralkyl-O—C=O group.

"Aryloxycarbonyl" denotes an aryl-O—C=O group.

"Carbalkoxy" denotes a carboxyl substituent which is esterified with an alcohol of the formula $C_nH_{2n+1}OH$, n being from 1 to approximately 6.

"Carbamoyl" denotes a

group. Alkylcarbamoyl and dialkylcarbamoyl mean that the nitrogen of the carbamoyl is substituted by one or two alkyl groups respectively.

"Alkoxyalkyl" denotes an alkyl group as described above which is substituted with an alkoxy group as described above.

Compounds of the above-defined general formula I are known and are described for example in U.S. Pat. No. 3,615,745.

In one preferred embodiment the compound or compounds according to the general formula I are selected from the group consisting of 4-tolyl diiodomethyl sulphone, phenyl diiodomethyl sulphone, 4-tolyl dibromomethyl sulphone, 4-tolyl tribromomethyl sulphone, 4-(methylamido)phenyl diiodomethyl sulphone, n-heptyl diiodomethyl sulphone, 4-aminophenyl diiodomethyl sulphone, 4-chlorophenyl diiodomethyl sulphone, 4-tert-butylphenyl diiodomethyl sulphone, 3-tolyl diiodomethyl sulphone, 2-tolyl-diiodomethyl sulphone, 4-bromophenyl diiodomethyl sulphone, 2-methyl-4-chlorophenyl diiodomethyl sulphone, α-naphthyl diiodomethyl sulphone, 2-methyl 4-bromophenyl diiodomethyl sulphone, 3-methyl-4-bromophenyl diiodomethyl sulphone, n-butyl diiodomethyl sulphone, benzyl diiodomethyl sulphone, 2,4-dimethylphenyl diiodomethyl sulphone, 3,4-dichlorophenyl diiodomethyl sulphone, 4-chlorophenyl dibromomethyl sulphone, 4-methoxyphenyl dibromomethyl sulphone, ethyl diiodomethyl sulphone, tert-butyl diiodomethyl sulphone, 4-chlorophenyl tribromomethyl sulphone, 4-methoxyphenyl tribromomethyl sulphone, benzyl iodomethyl sulphone, ethyl diiodomethyl sulphone, 2-methyl-4-tertbutylphenyl diiodomethyl sulphone, 2-nitro-4-methylphenyl dibromomethyl sulphone, 2-nitro-4-methylphenyl tribromomethyl sulphone, 3-tolyl tribromomethyl sulphone, 4-tert-butylphenyl bromomethyl sulphone, 2-nitro-4-methylphenyl iodomethyl sulphone, 4-chlorobenzyl diiodomethyl sulphone, 2-nitro-4-chlorophenyl iodomethyl sulphone, 2-nitro-4-chlorophenyl tribromomethyl sulphone, 4-nitrophenyl diiodomethyl sulphone, 2-methyl 4-tert-butylphenyl tribromomethyl sulphone, 2-nitro-4-chlorophenyl diiodomethyl sulphone, 2-isopropylphenyl bromomethyl sulphone, 2-isopropylphenyl diiodomethyl sulphone, 4-nitrophenyl tribromomethyl sulphone, 4-(2,2-dimethylpropyl)phenyl diiodomethyl sulphone, 4-chlorobenzyl diiodomethyl sulphone, cyclohexyl diiodomethyl sulphone, n-pentyl diiodomethyl sulphone, n-hexyl diiodomethyl sulphone, n-propyl diiodomethyl sulphone, n-octyl diiodomethyl sulphone, 4-methylbenzyl diiodomethyl sulphone, 4-fluorobenzyl diiodomethyl sulphone, 4-bromobenzyl diiodomethyl sulphone, 4-methoxybenzyl diiodomethyl sulphone, 3-chlorobenzyl diiodomethyl sulphone, 3,5-dimethyl diiodomethyl sulphone, 1-phenyl-2-(diiodomethylsulphonyl)ethane, 3-bromobenzyl diiodomethyl sulphone, 2-naphthylmethyl diiodomethyl sulphone, 1-phenyl-3-(diiodomethylsulphonyl)propane, isobutyl diiodomethyl sulphone, 3,4-dimethylbenzyl diiodomethyl sulphone, 3,3-dimethylpropyl diiodomethyl sulphone, 2,2,4,4-tetramethylbutyl diiodomethyl sulphone, 4-fluorobenzyl dibromomethyl sulphone, 3-chlorobenzyl dibromomethyl sulphone, 4-bromobenzyl dibromomethyl sulphone, 3,4-dichlorobenzyl dibromomethyl sulphone, 2,4-dichlorobenzyl dibromomethyl sulphone, 3-bromobenzyl dibromomethyl sulphone, 2-bromobenzyl dibromomethyl sulphone, 2-chlorobenzyl dibromomethyl sulphone, 4-methylbenzyl dibromomethyl sulphone, 2-methylbenzyl dibromomethyl sulphone, 3-methylbenzyl dibromomethyl sulphone, 4-nitrobenzyl dibromomethyl sulphone, 4-methoxybenzyl dibromomethyl sulphone, 2,5-dimethylbenzyl dibromomethyl sulphone, 3,4-dimethylbenzyl dibromomethyl sulphone, 1-phenyl-2-dibromomethylsulphonylethane, 1-phenyl-3-(dibromomethylsulphonyl)propane, cyclohexyl dibromomethyl sulphone, n-heptyl dibromomethyl sulphone, n-decyl dibromomethyl sulphone, n-hexadecyl dibromomethyl sulphone, 3-methylpropyl diiodomethyl sulphone and n-decyl diiodomethyl sulphone.

Halomethyl-substituted pyridine derivatives such as pyridines which are mono-, di- or tri-substituted by halomethyl groups at positions 2 and/or 4 and/or 6 of the pyridine ring, and the corresponding pyridine 1-oxides, examples being 2,6-bisdiiodomethylpyridine and 2,6-bisdiiodomethylpyridine 1-oxide, 2,6-bisiodomethylpyridine and 2,6-bisiodomethylpyridine 1-oxide, 2,6-bisdibromomethylpyridine and dibromomethylpyridine 1-oxide, 2,6-bisbromomethylpyridine and 2,6-bisbromomethylpyridine 1-oxide, 4-dibromomethylpyridine and 4-dibromomethylpyridine 1-oxide, 4-diiodomethylpyridine and 4-diiodomethylpyridine 1-oxide, 4-bromomethylpyridine and 4-bromomethylpyridine 1-oxide, 4-iodomethylpyridine and 4-iodomethylpyridine 1-oxide, and 4-bromonitromethylpyridine and 4-bromonitromethylpyridine 1-oxide. Further examples of halomethyl-substituted pyridine derivatives are the 2- and/or 4-halomethyl-substituted quinoline derivatives and quinoline 1-oxide and its derivatives.

Activated vinyl compounds and halovinyl compounds according to formula (II) such as, for example, vinylaldehydes, vinylcarboxylic acids, vinylsulphonic acid derivatives, 2-vinyl- and 4-vinylpyridine derivatives such as 2-vinylpyridine and 2-vinylpyridine 1-oxide, 4-vinylpyridine and 4-vinylpyridine 1-oxide, and (2-bromo-2-nitroethenyl)benzene.

Further suitable electrophiles (A) are N-(2-iodo-1-iodomethylethyl)benzenesulphonamide, allyl p-tolyl sulphone, 3-bromomethylpyridine hydrobromide and 3-bromomethylpyridine hydroiodide.

Additionally suitable as electrophiles (A) are acceptor-substituted activated aromatics which are capable of entering into nucleophilic substitution reactions, examples being 2,4,5,6-tetrachloro-1,3-dicyanobenzene(chlorothalonil), 2,3,5,6-tetrachloro-4-(methylsulphonyl)pyridine, 3,3,4,4-tetrachlorotetrahydro-1,1-dioxothiophene, 4,5-dichloro-3H-1,2-dithiol-3-one, 2,4-dichloro-6-(2-chloroaniline)-1,3,5-triazine.

Further suitable electrophiles (A) are dimethyl dicarbonate (DMDC), 1-iodo-2-propyn-1-ol (IPA), 1,1,2-triiodoprop-1-en-3-ol, iodoform, 3-iodopropargyl N-butylcarbamate (IPBC), 3-iodopropargyl N-phenylcarbamate (IPPC), 3-iodopropargyl carbamate (IPC), maleimide and maleimide derivatives, fulvenes and acceptor-substituted fulvene derivatives, and hydroxylamine-o-sulphonic acid.

Further suitable electrophiles (A) are phthalimide derivatives such as folpet and derivatives, fluorfolpet, captan and derivatives, captafol, sulphonamide compounds such as dichlofluanid and derivatives, tolylfluanid and derivatives, and also (methylthio)urea derivatives such as N-methyl-N'-(3,4-dichlorophenyl)-N'-(dichlorofluoromethylthio)urea.

Suitable inhibitor concentrations of the electrophilic compounds (A) are in the range from 1 to 1000 ppm, preferably in the range from 1 to 100 ppm, more preferably in the range from 1 to 25 ppm, and with more particular preference in the range from 1 to 10 ppm, based on the final concentration thereof in the container. In one particular embodiment the electrophilic compound is used in a ratio to the preservative of 1:1000 to 1000:1, preferably of 1:100 to 100:1, more preferably of 1:10 to 10:1.

Preferred electrophilic compounds (A) are iodoform, chlorothalonil, hydroxylamine-o-sulphonic acid, maleimide, 2,6-bisbromomethylpyridine 1-oxide, 2,6-bisdibromomethylpyridine 1-oxide, 2,6-bischloromethylpyridine, acetylacetone, diiodomethane, 2-dibromonitromethyl-3-methylpyridine, 2-iodo-1-propenyl phenyl sulphone, 3-iodomethylpyridine hydroiodide, 3-bromomethylpyridine hydrobromide, bromomethyl p-phenyl sulphone, 2-bromomethyl-6-methylpyridine, diiodomethyl p-tolyl sulphone, N-(2-iodo-1-iodomethyl-ethyl)benzylsulphonamide, N-trichloromethylthiophthalimide (folpet), dichlofluanid, allyl p-tolyl sulphone.

Particularly preferred electrophilic compounds (A) are iodoform, chlorothalonil, 3-iodomethylpyridine hydroiodide, 3-bromomethylpyridine hydrobromide, 2,6-bis-dibromomethylpyridine 1-oxide, diiodomethyl p-tolyl sulphone and N-(2-iodo-1-iodomethylethyl)benzylsulphonamide. It is of course also possible to use mixtures of the abovementioned electrophilic compounds (A) for preventing ghost odour.

In one embodiment of the invention the inhibitors from the group of electrophiles (A) selected from the group of formaldehyde, methylenebisthiocyanate, dibromocyanobutane, dibromonitrile propionamide and 2-bromo-2-nitropropane-1,3-diol (bronopol) are not embraced by the subject matter of the present invention.

Suitable nucleophilic compounds (B) are selected from thiols, dithio compounds, amines such as primary, secondary and tertiary amines, alkylamines, hydrazines, such as alkylhydrazines and phenylhydrazines, CH-acidic compounds, such as 1,3-diketo compounds, or geminal sulphone derivatives.

Suitable inhibitor concentrations for the nucleophilic compound or compounds are in the range from 1 to 1000 ppm, preferably in the range from 1 to 100 ppm and with more particular preference in the range from 1 to 10 ppm, based on the final concentration thereof in the container. In one particular embodiment the nucleophilic compound is used in a ratio to the preservative of 1000:1 to 1:1000, preferably of 100:1 to 1:100, more preferably of 10:1 to 1:10. Particularly preferred nucleophilic compounds are iodides such as sodium iodide or potassium iodide. It is of course also possible to use mixtures of the abovementioned nucleophilic compounds (B).

In one embodiment of the invention the inhibitors from the group of nucleophilic compounds (B) selected from the group of cysteine, thiosalicylic acid and amides thereof, mercaptobenzothiazole, sodium pyrithione and zinc pyrithione are not embraced by the subject matter of the present invention.

Suitable alkylating reagents (C) are compounds suitable for transferring unbranched or branched, substituted or unsubstituted $C_1$-$C_{10}$ alkyl groups, such as halocarboxylic acids such as, for example, α-halocarboxylic acids such as bromoacetic acid and iodoacetic acid, alkyl halides, methionine, benzyl halides, dialkyl ethers, diaryl ethers, acryloalkenyl ethers, alkyl sulphonates, with the exception of methyl para-toluenesulphonate. Suitable inhibitor concentrations for the alkylating reagent or alkylating reagents (C) are in the range from 1 to 1000 ppm, preferably in the range from 1 to 100 ppm and more preferably in the range from 1 to 10 ppm, based on the final concentration thereof in the container. In one particular embodiment the alkylating reagent is used in a ratio to the preservative of 1:1000 to 1000:1, preferably of 1:100 to 100:1, with particular preference of 1:10 to 10:1. It is of course also possible to use mixtures of the abovementioned alkylating agents (C).

In one embodiment of the invention methyl para-toluenesulphonate from the group of alkylating agents (C) is not embraced by the subject matter of the present invention.

For the purposes of the present invention, antioxidants (D), also referred to as oxidation inhibitors or antioxygens, are substances or compounds which reduce or even completely prevent changes in the coating composition that are caused by oxidative processes.

Examples of suitable antioxidants (D) are phenols substituted by sterically hindering groups. Phenols in the context of the present invention encompass substituted and unsubstituted phenols, hydroquinones, resorcinols and pyrocatechols and also their metal complexes. Excepted from the abovementioned compounds are resorcinol and also pyrogallol.

Suitable phenols are 1,3,5-tris(3,5-di-tert-butyl-4-hydroxybenzypisocyanurate, 1,3,5-tris[[4-tert-butyl-3-hydroxy-2,6-xylyl]methyl]-1,3,5-triazine-2,4,6(1H,3H,5H)-trione, 2-(1,1-dimethylethyl)-6-[[3-(1,1-dimethylethyl)-2-hydroxy-5-methylphenyl]methyl]-4-methylphenyl acrylate, 2,2',6,6'-tetra-tert-butyl-4,4'-methylenediphenol, 2,2'-ethylidenebis[4,6-di-tert-butylphenol], 2,2'methylene-bis[6-(1-methylcyclohexyl)-p-cresol], 2',3-bis[[3-[3,5-di-tert-butyl-4-hydroxyphenyl]propionyl]]propionyl hydrazide, 2,4-bis[(octylthio)methyl]-o-cresol, 2,4-di-tert-butylphenol, 2,5-di-tert-butylhydroquinone, 2,5-di-tert-pentylhydroquinone, 2,6-di-tert-butyl-4-nonylphenol, 2,6-di-tert-butyl-p-cresol (butylated hydroxytoluene, BHT), 2,6-di-tert-butylphenol, 2,6-di-tert-butyl-α-dimethylamino-p-cresol, 3,3',3'',5,5',5''-hexa-tert-butyl-α,α',α''-(mesitylene-2,4,6-triyptri-p-cresol, 4,4',4''-(1-methylpropanyl-3-ylidene)tris[6-tert-butyl-m-cresol], 4-sec-butyl-2,6-di-tert-butylphenol, phenol, 4,4'-(1-methylethylidene)bis-, reaction products with isobutylene and styrene, diethyl[[3,5-bis(1,1-dimethylethyl)-4-hydroxyphenyl]methyl]phosphonate, 4-(2-methylprop-2-enyl)phenol, 6,6'-di-tert-butyl-2,2'-methylenedi-p-cresol, 6,6'-di-tert-butyl-2,2'-thiodi-p-cresol, 6,6'-di-tert-butyl-4,4'-butylidenedi-m-cresol, 6,6'-di-tert-butyl-4,4'-diethyl-2,2'-methylenediphenol, 6,6'-di-tert-butyl-4,4'-thiodi-m-cresol, 6-tert-butyl-2,4-xylenol, 2-tert-butylhydroquinone, calcium diethyl bis [[[3,5-bis(1,1-dimethylethyl)-4-hydroxyphenyl]methyl]phosphonate], ethylenebis[3,3-bis(3-tert-butyl-4-hydroxyphenyl)butyrate], ethylenebis(oxyethylene)bis [3-(5-tert-butyl-4-hydroxy-m-tolyl)propionate], hexamethylenebis[3-(3,5-di-tert-butyl-4-hydroxyphenyl)-propionate], hydroquinone monomethyl ether, isotridecyl 3-(3,5-di-tert-butyl-4-hydroxyphenyl)propionates, N,N'-hexane-1,6-diylbis[3-(3,5-di-tert-butyl-4-hydroxyphenyl)propionamide], N,N'-propane-1,3-diylbis[3-(3,5-di-tert-butyl-4-hydroxyphenyl) propionamide, octadecyl 3-(3,5-di-tert-butyl-4-hydroxyphenyl)propionates, pentaerythrityl tetrakis(3-(3,5-di-tert-butyl-4-hydroxyphenyl)propionate),
phenol, 4-methyl, reaction products with dicyclopentadiene and isobutylene, phenol, styrenized, thiodiethylenebis[3-(3,5-di-tert-butyl-4-hydroxyphenyl)propionate], tris(1-phenylethyl)phenol, 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(γ-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chain, for example 2,6-dinonyl-4-methylphenol, 2,4-dimethyl-6-(1'-methylundec-1'-yl) phenol, 2,4-dimethyl-6-(1'-methylheptadec-1'-yl)phenol, 2,4-dimethyl-6-(1'-methyltridec-1'-yl)phenol, butylated hydroxyanisole (BHA), 2,4-dioctylthiomethyl-6-tert-butylphenol, 2,4-dioctylthiomethyl-6-methylphenol, 2,4-dioctylthiomethyl-6-ethylphenol, 2,6-didodecylthiomethyl-4-nonylphenol, 2,6-di-tert-butyl-4-methoxyphenol, 2,5-di-tert butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butylhydroquinone, o-phenylphenol, 3,5-di-tert-butyl-4-hydroxyanisole, 3,5-di-tert-butyl-4-hydroxyphenyl stearate, bis(3,5-di-tert-butyl-4-hydroxyphenyl)adipate.

Further suitable antioxidants are tocopherols, such as δ-tocopherol, β-tocopherol, γ-tocopherol, σ-tocopherol and mixtures thereof (vitamin E), and also extracts containing tocopherol, hydroxylated thiodiphenyl ethers, such as 2,2'-thiobis(6-tert-butyl-4-methylphenol), 2,2'-thiobis(4-octylphenol), 4,4'-thiobis(6-tert-butyl-3-methylphenol), 4,4'-thio-bis(6-tert-butyl-2-methylphenol), 4,4'-thiobis(3,6-di-sec-amylphenol), 4,4'-bis(2,6-dimethyl-4-hydroxyphenyl)disulphide, alkylidenebisphenols, such as 2,2'-methylenebis(6-tert-butyl-4-methylphenol), 2,2'-methylenebis(6-tertbutyl-4-ethylphenol), 2,2'-methylenebis[4-methyl-6-(α-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)4-nonylphenol], 2,2'-methylenebis[6-(α,α- dimethylbenzyl)-4-nonylphenol], 4,4'-methylenebis(2, 6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl)butyrate], bis(3-tert-butyl-4-hydroxy-5-methylphenyl)dicyclopentadiene, bis[2-(3'-tert-butyl-2'-hydroxy-5'-methylbenzyl)-6-tert-butyl-4-methylphenyl]terephthalate, 1,1-bis(3,5-dimethyl-2-hydroxyphenyl)butane, 2,2-bis(3,5-di-tert-butyl-4-hydroxyphenyl)propane, 2,2-bis(5-tert-butyl-4-hydroxy-2-methylphenyl)-4-n-dodecylmercaptobutane, 1,1,5,5-tetra-(5-tert-butyl-4-hydroxy-2-methylphenyl)pentane, O-, N- and S-benzyl compounds, such as 3,5,3',5'-tetra-tert-butyl-4,4'-dihydroxydibenzyl ether, octadecyl 4-hydroxy-3,5-dimethylbenzylmercaptoacetate, tridecyl 4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithio-terephthalate, bis(3,5-di-tert-butyl-4-hydroxybenzyl)sulphide, isooctyl 3,5-di-tert-butyl-4-hydroxybenzylmercaptoacetate, hydroxybenzylated malonates, such as dioctadecyl-2,2-bis(3,5-di-tert-butyl-2-hydroxybenzyl)malonate, dioctadecyl-2-(3-tert-butyl-4-hydroxy-5-methylbenzyl)malonate, didodecylmercaptoethyl 2,2-bis(3,5-di-tert-butyl-4-hydroxybenzyl)-malonate, bis[4-(1,1,3,3-tetramethylbutyl)phenyl]2,2-bis(3,5-di-tert-butyl-4-hydroxybenzyl)malonate, aromatic hydroxybenzyl compounds, such as 1,3,5-tris(3,5-di-tert-butyl-4-hydroxybenzyl)-2,4,6-trimethylbenzyl, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol, triazine compounds, such as 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)-1,2,3-triazine, 1,3,5-tris-(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropioyl)hexahydro-1,3,5-triazine, 1,3,5-tris(3,5-dicyclohexyl-4-hydroxybenzyl)isocyanurate, 2-tert-butyl-4-cyclopropyl-6-(methylthio)-1,3,5-triazine-2,4-diyldiamine, acylaminophenols, such as 4-hydroxylauranilide, 4-hydroxystearanilide, octyl N-(3,5-di-tert-butyl-4-hydroxyphenyl)carbamate, esters of β-(3,5-di-tert-butyl-4-hydroxyphenyl)propionic acid with monohydric or polyhydric alcohols, such as with methanol, ethanol, n-octanol, isooctanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(bydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane, very particular suitability being possessed by, and preference given to, the ester with octadecanol (IRGANOX 1076® from Ciba Spec.), esters of β-(5-tert-butyl-4-hydroxy-3-methylphenyl)propionic acid with monohydric or polyhydric alcohols, such as with methanol, ethanol, n-octanol, isooctanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethypoxamide, 3-thiaundecanol, 3-thiapentadecanol, trimethylhexanediol, trimethylolpropane, 4-hydroxymethyl-1-phospha-2,6,7-trioxabicyclo[2.2.2]octane, esters of β-(3,5-dicyclohexyl-4-hydroxyphenyl)propionic acid with monohydric or polyhydric alcohols, such as with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane, esters of 3,5-di-tert-butyl-4-hydroxyphenylacetic acid with monohydric or polyhydric alcohols, such as with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

Amides of β-(3,5-di-tert-butyl-4-hydroxyphenyl)propionic acid, e.g. N,N'-bis(3,5-di-tert-butyl-4-hydroxyphenylpropionyl)hexamethylenediamide, N,N'-bis(3,5-di-tert-butyl-4-hydroxyphenylpropionyl)trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl]oxamide (Naugard® XL-1 from Uniroyal), ascorbic acid (vitamin C), isoascorbic acid and also compounds and salts of ascorbic acid and isoascorbic acid, such as sodium ascorbate, calcium ascorbate, ascorbyl palmitate, ascorbyl stearate, sodium isoascorbate, calcium isoascorbate, aminic antioxidants, such as N,N'-diisopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulphamoyl)-diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl) amine, 2,6-di-tert-butyl-4-dimethylaminoethylphenol, 2,4'-di-aminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)propane, o-tolyl)biguanide, bis[4-(1', 3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octylphenothiazines, N-allylphenothiazine, N,N,N',N'-tetraphenyl-1,4-diaminobut-2-ene, N,N-bis(2,2,6,6-tetramethylpiperid-4-yl)hexamethylenediamine, bis(2, 2,6,6-tetramethylpiperid-4-yl) sebacate, 2,2,6,6-tetramethylpiperidin-4-one, 2,2,6,6-tetramethylpiperidin-4-ol, 1,4-benzenediamine, N,N'-mixed phenyl and toluene derivatives, 4'-anilinotoluene-4-sulphoanilide, 4-(1-methyl-1-phenylethyl)-N-[4-(1-methyl-1-phenylethyl)phenyl]anilines, benzenamine, 2-ethyl-N-(2-ethylphenyl)-, tripropenyl derivatives, benzenamine, N-{4-[(1,3-dimethylbutypimino]-2,5-cyclohexadien-1-ylidine}, benzeneamine, N-phenyl-, reaction products with 2,4,4-trimethylpentene, bis(4-octylphenyl)amine, diphenylamine, low-temperature-reaction products of diphenylamines and -acetone, ethoxyquin, N-1-naphthylaniline, N-1,3-dimethylbutyl-N'-phenyl-p-phenylenediamine, N-isopropyl-N-phenyl-p-phenylenediamine, N,N'-bis(1,4-dimethylpentyl)-p-phenylenediamine, N,N'-di-2-naphthyl-p-phenylenediamine, N,N'-di-sec-butyl-p-phenylenediamine, N,N'-diphenyl-p-phenylenediamine, polymerized 1,2-dihydro-2,2,4-trimethylquinoline.

Thiosynergists such as dilauryl thiodipropionate and/or distearyl thiodipropionate.

Phosphorus compounds such as orthophosphoric acid, phosphates, sodium orthophosphoric acid, monosodium phosphate, disodium phosphate, tri-sodium phosphate, potassium orthophosphoric acid, monopotassium orthophosphate, dipotassium orthophosphate, tripotassium orthophosphate, calcium orthophosphoric acid, monocalcium orthophosphate, dicalcium orthophosphate, tricalcium orthophosphate, 2,4,6-tri-t-butylphenyl-2-butyl-2-ethyl-1,3-propanediol phosphate, 3,9-bis(2,4-di-tert-butylphenoxy)-2,4,8,10-tetraoxa-3,9-diphosphaspiro[5.5]undecane, bis(2,4-dicumylphenyl) pentaerythritol diphosphite, bis(2,4-di-tert-butyl-6-methylphenyl)ethyl phosphate, isodecyl diphenyl phosphite, isooctyl diphenyl phosphite, O,O'-dioctadecylpentaerythritol bis(phosphite), phosphorus trichloride, reaction products with 1,1'-biphenyl and 2,4-bis(1, 1-dimethyl) phenol, tetralcis(2,4-di-tert-butylphenyl) [1,1-biphenyl]-4,4'-diyl bisphosphonite, tributyl phosphite, tridodecyl phosphite, triisodecyl phosphite, triphenyl phosphite, tris(2,4-ditert-butylphenyl)phosphite, tris(nonylphenyl) phosphite, tris[4,4'-thiobis[3-methyl-6-tert-butylphenol]]phosphite, lecithin thioesters such as 2,2-bis[[3-(dodecylthio)-1-oxopropoxy] methyl]propane-1,3-diyl bis[3-(dodecylthio)propionate], di(tridecyl) 3,3'-thiodipropionate, didodecyl 3,3'-thiodipropionate, dioctadecyl 3,3'-thiodipropionate, ditetradecyl 3,3'-thiobispropionate, metal thiolates such as 1,3-dihydro-4(or -5)-methyl-2H-benzimidazole-2-thione, zinc salt (2:1), bis(diisobutyldithiocarbamato)nickel, nickel bis(dibutyldithiocarbamate), zinc bis(dibutyldithiocarbamate), zinc di(benzimidazol-2-yl)disulphide, further sulphur compounds such as dioctadecyl disulphide, 1,3-dihydro-4(or -5)-methyl-2H-benzimidazol-2-thione, benzimidazol-2-thiol, gallic acid and compounds and salts of gallic acid such as propyl gallate, octyl gallate, dodecyl gallate, lactic acid, citric acid, tartaric acid, metatartaric acid, and compounds and salts of these compounds, such as sodium lactate, potassium lactate, calcium lactate, sodium citrate, potassium citrate, calcium citrate, ammonium citrate, tartaric acid and tartrates, mono- and di-tartrates, potassium tartrates, tartar, sodium potassium tartrate, calcium tartrate, sulphur dioxide, sulphurous acid and its salts, and also sodium sulphite, sodium bisulphite, sodium disuiphite, potassium sulphite, calcium sulphite, calcium hydrogen sulphite, potassium bisulphite, carotenoids selected from astaxanthin, β-carotene, canthaxanthin, capsanthin, capsorubin, cryptoxanthin, luteine, luteoxanthin, lycopine, zeaxanthin, polyphenols, such as flavonoids and anthocyans selected from quercetin, rutin, kaempferol, myricetin, isorhamnetin, luteolin, apigenin, morin, catechin, gallocatechin, epicatechin, epigallocatechin gallate, theaflavin, thearubigin, hesperetin, naringenin, eriodictyol, taxifolin, genisteine, daidzenin, licoricidin, cyanidin, delphinidin, malvidin, pelargonidin, peonidin, petunidin, malonic acid, adipic acid and compounds and salts of malonic acid and adipic acid, such as sodium malate, potassium malate, calcium malate, sodium adipate, potassium adipate, calcium adipate, further antioxidants such as succinic acid, calcium disodium ethylenediaminetetraacetate, tin(II) chloride, glutathione and selenium.

Antioxidative enzymes such as superoxide dismutase, glutathione peroxidase and catalase.

Further suitable antioxidants are particularly unsaturated hydrocarbons such as unsaturated resins. In the context of the present invention, it is possible with preference to use natural and modified resins, examples being gum resins, colophony resins, oil resins, distilled resins, hydrogenated resins, and dimerized and polymerized resins. Additionally use may also be made of esters, especially glycerol or pentaerythritol esters of natural or modified resins, particularly glycerol esters of wood resins, glycerol esters of hydrogenated resins or the like; furthermore, it is also possible to employ aliphatic, aromaticor mixed aliphatic or aromatic hydrocarbon resins and phenolically modified terpene resins or their hydrogenated derivatives. For particular applications it is of course also possible to use mixtures of the stated tackifiers.

Among the aforementioned compounds several compounds are known to the person skilled in the art as tackifiers. These Tackifiers are according to a preferred embodiment of the invention selected from the group consisting of aliphatic and aromatic hydrocarbon-resins, polymers of aliphatic $C_5$-piperinyl-resins or aromatic $C_9$-resins, colophony resins, and linseed oil.

A preferred antioxidant for use with particular reference in the context of the invention is Foral™ 85-E from Eastman™, an ester of a hydrogenated resin, or Tacolyn™ 100 Resin Dispersion from Eastman™.

The aforementioned antioxidants can be used alone or in a mixture with an antioxidant or two or more antioxidants.

Suitable inhibitor concentrations for the antioxidant (D) are in the range from 1 to 10.000 ppm, preferably in the range from 1 to 5.000 ppm, and with more particular preference in the range from 1 to 1.000 ppm, and with more particular preference in the range from 1 to 500 ppm, based on its final concentration in the container. In one particular embodiment the antioxidant (D) is used in a ratio to the preservative of 1:1000 to 1000:1, preferably of 1:100 to 100:1, more preferably of 1:10 to 10:1.

Particularly suitable antioxidants are butylated hydroxytoluene (BHT), butylated hydroxyanisole (BHA), 2,5-di-tert-butylhydroquinone, 3,5-di-tert-butylhydroquinone, propyl gallate, ascorbic acid and isoascorbic acid.

In one embodiment of the invention the odour preventative (D) is selected from the group consisting of 2,5-di-tertbutylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butylhydroquinone, o-phenylphenol, 3,5-di-tert-butyl-4-hydroxyanisole, 3,5-di-tert-butyl-4-hydroxyphenyl stearate, bis(3,5-di-tert-butyl-4-hydroxyphenyl) adipate.

The invention further provides a coating composition containing 10 to 1,000 ppm of 2-methyl-4-isothiazolin-3-one and/or 10 to 1,000 ppm of 2-n-octyl-4-isothiazolin-3-one, and also 200 to 1,000 ppm of one or more odour preventatives selected from the group consisting of 2,5-di-tertbutylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butylhydroquinone, o-phenylphenol, 3,5-Di-tert-butyl-4-hydroxyanisole, 3,5-di-tert-butyl-4-hydroxyphenyl stearate, bis(3,5-di-tert-butyl-4-hydroxyphenyl) adipate. In a further embodiment the invention provides an interior or exterior emulsion paint which comprises the titanium dioxide, 10 to 1,000 ppm of 2-methyl-4-isothiazolin-3-one and/or 10 to 1,000 ppm of 2-n-octyl-4-isothiazolin-3-one and 1 to 1,100 ppm, preferably 9 to 510 ppm and more preferably 9 to 210 ppm of one or more odour preventatives selected from the group consisting of 2,5-di-tertbutylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butylhydroquinone, o-phenylphenol, 3,5-di-tert-butyl-4-hydroxyanisole, 3,5-di-tert-butyl-4-hydroxyphenyl stearate, bis(3,5-di-tert-butyl-4-hydroxyphenyl)adipate. Advantageously by this means it is possible to reduce not only the graying of the emulsion paint but also the occurrence of ghost odour.

Oxidizing agent(s) in accordance with the present invention are understood to be compounds which are able to oxidize other compounds and are themselves reduced in the process. Oxidizing agents may accept electrons, while the reducing agents give them up. Suitable oxidizing agents (E) are compounds selected from the group of bromates, iodates, such as sodium and potassium iodate, and sodium and potassium bromate, and sodium and potassium bromite, peroxides, hydrogen peroxide, zinc peroxide, benzoyl peroxide, potassium peroxide, sodium perborate, potassium perborate, sodium persulphate, sodium percarbonate, sodium hypochlorite, ammonium hypochlorate, potassium percarbonate, ammonium percarbonate, ammonium persulphate, potassium persulphate, tert-butyl hydroperoxide, magnesium monoperoxyphthalates, sodium peroxides, urea hydrogen peroxides, magnesium peroxides, calcium peroxides, sodium perborate, sodium perborate tetrahydrate, peroxyacetic acid, halogens and halogen-releasing compounds, chlorine, sodium hypochlorite, calcium hypochlorite, hypobromous acid, chlorine dioxide, chloramine-T, dichloroisocyanuric acid and its sodium salt, trichloroisocyanuric acid, trichloromelamine (TCM), N-chlorosuccinimide (NCS), N-bromosuccinimide (NBS), 1,3-dichloro-5,5-dimethylhydanto in (DCDMH), 1-bromo-3-chloro-5,5-dimethylhydantoin (BCDMH), poly(vinylpyrrolidone)iodide, sodium iodate. In general the inhibitor concentration in the case of potassium bromate is in the range from 1 to 1,000 ppm, preferably being 1 to 100 ppm.

Suitable inhibitor concentrations for the oxidizing agent (E) are in the range from 1 to 1000 ppm, preferably in the range from 1 to 100 ppm and more preferably in the range from 1 to 10 ppm, based on its final concentration in the container. In one particular embodiment the oxidizing agent (E) is used in a ratio to the preservative of 1:1000 to 1000:1, preferably of 1:100 to 100:1, more preferably of 1:10 to 10:1.

In one embodiment of the invention, resorcinol and pyrogallol from the group of the oxidants (E) are not encompassed by the subject matter of the present invention.

In accordance with the present invention it is possible to use a single inhibitor or else two or more inhibitors to prevent the occurrence of ghost odour. When two or more inhibitors are used, they can come from two or more of groups A, B, C, D or E, or only from one of the groups. The combination of inhibitors from group E with inhibitors from group D is less preferred in this context. In the case of combinations of inhibitors, the concentrations indicated above may possibly turn out to be lower than the values stated. The reason for this may be synergism among the individual inhibitors.

The invention further provides coating compositions comprising methyl-4-isothiazolin-3-one and/or octyl-4-isothiazolin-3-one and also one or more inhibitors selected from the group consisting of iodoform, chlorothalonil, hydroxylamine-o-sulphonic acid, maleimide, 2,6-bis-bromomethylpyridine 1-oxide, 2,6-bisdibromomethylpyridine 1-oxide, 2,6-bis-chloromethylpyridine, acetylacetone, diiodomethane, 2-dibromonitromethyl-3-methylpyridine, 2-iodo-1-propenyl phenyl sulphone, 3-iodomethyl-pyridine hydroiodide, 3-bromomethylpyridine hydrobromide, bromomethyl p-phenyl sulphone, 2-bromomethyl-6-methylpyridine, diiodomethyl p-tolyl sulphone, N-(2-iodo-1-iodomethylethyl)benzylsulphonamide, N-trichloromethylthiophthalimide, dichlofluanid, allyl p-tolyl sulphone, sodium iodide, potassium iodide, bromoacetic acid, iodoacetic acid, alkyl halides, methionine, benzyl halides, dialkyl ethers, diaryl ethers, acryloalkenyl ethers, alkyl sulphonates, butylated hydroxytoluene (BHT), butylated hydroxyanisole (BHA), 2,5-di-tert-butylhydroquinone, 3,5-di-tert-butylhydroquinone, propyl gallate, ascorbic acid, isoascorbic acid, potassium iodate, sodium iodate and potassium bromate.

Coating compositions of the invention, for the purposes of the invention also called containers, which represent one storage form of the coating compositions, are, for example, solvent- or water-based coating materials for interior and/or exterior, such as renders, primers, wax emulsions and adhesives/sealants, and also paint compositions such as lime paints, size colours, mineral paints, natural paints, varnishes, stains, emulsion paints, latex paints, dispersion-based paints, and also starting materials and raw materials for producing such coating compositions, such as latices, polymer dispersions and resin dispersions.

Preferred coating compositions of the invention are water-based coating materials for interior and exterior such as renders, primers, wax emulsions and paint compositions such as lime paints, size colours, mineral paints, natural paints, varnishes, stains, emulsion paints, latex paints, dispersion-based paints, and also starting materials and raw materials for producing such coating compositions, such as latices, polymer dispersions and resin dispersions.

Particularly preferred coating compositions of the invention are aqueous paint compositions for interiors, such as emulsion paints and latex paints.

The coating compositions of the invention comprise known ingredients familiar to the skilled person. These are, for example, thickeners, defoamers, substances for setting and buffering the pH, fragrances, dispersing assistants, and colouring or discolouration-preventing substances, complexing agents and stabilisers.

The solvent used for preparing the coating composition is one selected from the group consisting of water, aliphatic alcohols having 1 to 4 carbon atoms, such as ethanol and isopropanol, a glycol, such as ethylene glycol, diethylene glycol, 1,2-propylene glycol, dipropylene glycol and tripropylene glycol, a glycol ether, such as butylglycol and butyldiglycol, a glycol ester, such as butylglycol acetate or 2,2,4-trimethylpentanediol monoisobutyrate, a polyethylene glycol, a propylene glycol, N,N-dimethylformamide or a mixture of two or more thereof. The polar liquid medium is more particularly water and/or glycol.

To formulate and/or stabilize the coating compositions it is possible to use dispersing assistants that are known to the skilled person, such as dispersing, water-soluble polymers (generally polyanions) such as polyacrylic acids with a molecular weight of 1,000 to 100,000 or copolymers of acrylic acid with maleic anhydride, having a molecular weight of 1,000 to 100,000, aromatic sulphonic acid condensates such as phenolsulphonic acid, naphthalenesulphonic acid with formaldehyde, and also silicone resins. Additionally it is possible for stabilizers such as xanthans, modified celluloses, such as methylcellulose, polyurethane thickeners and also silica to be present. Likewise present may be wetting agents known to the skilled person, such as dioctyl sulphosuccinate, $C_{10}$ to $C_{13}$ fatty alcohol ethoxylates, EO/PO block polymers, sulphonates, and also defoamers such as silicone defoamers, and fillers, such as talc, kaolins, titanium dioxide, silicates, fumed silica and/or zeolites.

Coating compositions typically also comprise one or more of the abovementioned preservatives. Preservatives are typically present in the coating composition in total concentrations in total concentrations of 1 to 3000 ppm. It is of course also possible for higher or lower concentrations of the preservative to be present. The coating composition of the invention may comprise one or more inhibitors. Where two or more inhibitors are present in the coating composition they may be selected from the same groups or from different groups of the abovementioned inhibitors.

The ratio of the total concentration of inhibitors used to the total concentration of preservatives used in the coating composition of the invention is in the range from 1000:1 to 1:1000, preferably in the range from 100:1 to 1:100, more preferably in the range from 10:1 to 1:10. In one embodiment of the invention the inhibitor or inhibitors is or are present in the coating composition in a concentration which is below their active concentration in the coating composition, i.e., at this concentration they make no contribution to preservation. Particular preference is given to inhibitor concentrations in the range from 5 to 15 ppm, based on their final concentration in the coating composition.

In one preferred embodiment the coating composition of the invention comprises 2-methyl-4-isothiazolin-3-one and/ or octyl-4-isothiazolin-3-one and also iodoform and/or diiodomethyl p-tolyl sulphone at concentrations in the range from 1 to 10,000 ppm, preferably in the range from 1 to 1000 ppm and more preferably in the range from 1 to 100 ppm.

The invention further provides a biocidal composition comprising 2-methyl-4-isothiazolin-3-one and/or octyl-4-isothiazolin-3-one and also one or more inhibitors selected from the group consisting of the above-defined (A) electrophilic compound(s), (B) nucleophilic compound(s), (C) alkylating agent(s), (D) antioxidants and (E) oxidizing agent(s).

In one embodiment of the invention the biocide composition comprises methyl-4-isothiazolin-3-one and/or octyl-4-isothiazolin-3-one. The ratio of inhibitor to N-alkylisothiazolinone in this case is generally in the range from 1000:1 to 1:1000.

It is judicious if the biocide composition of the invention is present for the purpose of application in combination with a polar or apolar liquid medium.

Preferred polar liquid media are water, aliphatic alcohols having 1 to 4 carbon atoms, for example ethanol and isopropanol, a glycol, for example ethylene glycol, diethylene glycol, 1,2-propylene glycol, dipropylene glycol and tripropylene glycol, a glycol ether, such as butylglycol and butyldiglycol, a glycol ester, such as butylglycol acetate or 2,2,4-trimethylpentanediol monoisobutyrate, a polyethylene glycol, a propylene glycol, N,N-dimethylformamide or a mixture of two more such media. The polar liquid medium is more particularly water and/or glycol.

Examples of apolar liquid media that can be used include aromatics, preferably xylene and toluene, which as well can be used alone or as mixtures of two or more such media.

The biocide composition of the invention may also be combined simultaneously with a polar or an apolar liquid medium.

The biocide composition of the invention is adjusted in its pH generally to a pH of 4 to 7, preferably to a value of 5 to 7.

The invention further provides a process for producing the coating composition of the invention, and also for suppressing ghost odour. According to the process of the invention, the inhibitor or inhibitors may be added at any point in time in the preparation of known coating compositions or adhesives, familiar to the skilled person, from the prior art. In the case of a paint composition from the prior art, the inhibitor or inhibitors is or are preferably incorporated by mixing, at the end of the operation for producing the paint composition from the prior art, or into the completed paint composition from the prior art.

The addition of the inhibitor or inhibitors may in this case take place individually or combination with the preservative or preservatives. Preferably the inhibitor or inhibitors is or are added in combination with the preservative or preservatives.

In one alternative embodiment the invention provides for the use of one or more of the above-defined inhibitors to prevent ghost odour in coating compositions which comprise methyl-4-isothiazolin-3-one and/or octyl-4-isothiazolin-3-one as preservatives, the coating compositions being free from 5-chloro-2-methylisothiazolin-3-one (CMIT). This means that CMIT is present in the coating composition in an amount of less than or equal to 5% by weight, preferably less than or equal to 2% by weight, more preferably less than 0.1% by weight, more particularly less than or equal to 0.01% by weight. It is also possible for there to be no CMIT present (i.e., it cannot be detected by the usual analytical methods). In this embodiment the invention likewise provides the above-defined biocide compositions and coating compositions which comprise the inhibitors of the invention and are free from 5-chloro-2-methylisothiazolin-3-one (CMIT). This means that CMIT is present in the coating composition or biocide composition in an amount of less than or equal to 5% by weight, preferably less than or equal to 2% by weight, more preferably less than 0.1% by weight, more particularly less than or equal to 0.01% by weight. It is also possible for there to be no CMIT present (i.e., for it to be unable to be detected with the usual analytical methods).

The invention is illustrated by the example below:

EXAMPLE

The following experiments were carried out using a silk matt paint with the composition specified in Table 1. The preservative used was 2-methyl-4-isothiazolin-3-one (Kordek® MLX, 9.7% MIT, Rohm & Haas).

TABLE 1

Composition of the paint

| Raw material | Identification | Manufacturer/ Supplier | Amount (g) | % |
|---|---|---|---|---|
| Water | — | — | 872 | 7.50 |
| Cellulose ether | Hydroxyethylcellulose | Hercules | 12 | 0.25 |
| Dispersant | Tamol 1124 | Rohm & Haas | 12 | 0.30 |
| Defoamer | LB-8041/4 | HI-MAR Specialties | 10 | 0.25 |
| Ammonium hydroxide | | Fisher Scientific | 2 | 0.10 |
| Calcium carbonate | HuberCarb Q325 | Huber | 312 | 7.80 |
| Titanium dioxide | Tiona 596 | Millenium | 624 | 15.60 |
| Propylene glycol | | Fisher Scientific | 72 | 1.80 |
| Koalescer | Texanol | Ashland Chemical | 60 | 1.50 |
| Acrylate dispersion | Rhoplex AC 264 | Rohm & Haas | 2024 | 50.60 |
| | | Total | 4000 | 100.00 |

The paint is admixed with the amount of MIT specified in Table 2, and homogenized subsequently the inhibitors under investigation are weighed in. A sample solely with MIT as the only additive, without inhibitors, serves as a positive control. A blank sample without MIT serves as a reference sample.

The liquid paint samples thus prepared are divided into three series. The coarse series A is applied immediately after preparation to glass slides and is dried at room temperature and 60%+/−10% relative humidity for 24 hours in order to produce a paint film. Sample series B is stored in a closed vessel at 40° C. in the wet state for 14 days. Sample series C is stored in a closed vessel at 40° C. in the wet state for 28 days. When storage is at an end, a paint film is produced from samples series B and sample series C in the same way as for sample series A.

The dried paint films are peeled from the glass slide and placed in a dish or watchglass. Subsequently the dried coating materials are treated with ozone in a desiccator which is connected to a waterjet pump (Brand, suction output about 500 l/h). This is done by passing the air that enters the desiccator via an ozone generator (ozone generator COM-SD-30, capacity 30 mg ozone/h, Anseros). Ozonization takes place at room temperature with a relative humidity of 60% of +/−10% over a period of 1 minute. Then the sample vessels are removed and the sample material is investigated by olfactory means for typical odour.

For the olfactory evaluation, a panel of five testers was selected, and evaluated the intensity of the odour from each individual sample. The testers were familiar with the typical ghost odour and on the basis of their knowledge were capable of classifying it unambiguously.

The intensity of the odour of the individual samples is investigated by all of the members of the panel, without knowing which samples were test samples and which samples were control samples, and the number of points that the other panel members had awarded, by summing each sample and giving it a number of points. The evaluation scale for the strength/intensity of the odour, with 0 standing for no odour at all and 3 for strong odour, is shown below:

| Number of points | Degree of odour |
|---|---|
| 0 | no odour |
| 1 | indefinite slight odour |
| 2 | slight but unambiguous odour |
| 3 | strong |

An average is formed from the numbers of points awarded by the testers to each sample. In order to ensure that the selection of the group is satisfactory to carry out the test, the rounded average of the samples without MIT ought not to exceed a figure of 0, and the rounded average of sample series B and C with MIT and without inhibitor ought not to be below a value of 2. If these criteria were not met, a new group was assembled. From the evaluations of the five testers, the average was formed and was rounded to a whole number. The results are shown in Table 2.

The results shown in Table 2 clearly indicate the concentration dependency and time dependency of the ghost odour.

TABLE 2

Results of odour tests after ozonization of the dried paint film

| Batch | Inhibitor | Amount of Inhibitor | Odour Sample series (A) | Odour Sample series (B) | Odour Sample series (C) |
|---|---|---|---|---|---|
| no MIT | none | — | 0 | 0 | 0 |
| +125 ppm MIT | none | — | 0 | 0 | 1 |
| +250 ppm MIT | none | — | 0 | 1 | 2 |
| +500 ppm MIT | none | — | 1 | 3 | 3 |
| +1000 ppm MIT | none | — | 1 | 3 | 3 |
| +500 ppm MIT | butylated hydroxytoluene BHT | 500 ppm | 0 | 0 | 1 |
| +500 ppm MIT | butylated hydroxyanisole BHA | 300 ppm | 0 | 0 | 1 |
| +500 ppm MIT | 2,5-di-tert-butylhydroquinone | 500 ppm | 0 | 1 | 1 |

TABLE 2-continued

Results of odour tests after ozonization of the dried paint film

| Batch | Inhibitor | Amount of Inhibitor | Odour Sample series (A) | Odour Sample series (B) | Odour Sample series (C) |
|---|---|---|---|---|---|
| +500 ppm MIT | 3,5-di-tert-butylhydroquinone | 500 ppm | 0 | 1 | 1 |
| +500 ppm MIT | propyl gallate | 300 ppm | 0 | 0 | 1 |
| +500 ppm MIT | ascorbic acid | 500 ppm | 0 | 1 | 1 |
| +500 ppm MIT | isoascorbic acid | 500 ppm | 0 | 1 | 1 |
| +500 ppm MIT | potassium iodide | 100 ppm | 0 | 0 | 0 |
| +500 ppm MIT | potassium iodate | 10 ppm | 0 | 0 | 0 |
| +500 ppm MIT | potassium bromate | 100 ppm | 0 | 0 | 1 |
| +500 ppm MIT | iodoform | 10 ppm | 0 | 0 | 0 |
| +500 ppm MIT | chlorothalonil | 100 ppm | 0 | 0 | 1 |
| +500 ppm MIT | hydroxylamine-o-sulphonic acid | 500 ppm | 0 | 1 | 2 |
| +500 ppm MIT | maleimide | 500 ppm | 0 | 1 | 2 |
| +500 ppm MIT | 2,6-bisbromomethyl-pyridine 1-oxide | 500 ppm | 0 | 0 | 0 |
| +500 ppm MIT | 2,6-bisdibromomethyl-pyridine 1-oxide | 500 ppm | 0 | 0 | 0 |
| +500 ppm MIT | 2,6-bischloromethylpyridine | 500 ppm | 0 | 1 | 1 |
| +500 ppm MIT | acetylacetone | 500 ppm | 0 | 1 | 2 |
| +500 ppm MIT | diiodomethane | 100 ppm | 0 | 0 | 1 |
| +500 ppm MIT | 2-dibromonitromethyl-3-methylpyridine | 500 ppm | 0 | 1 | 2 |
| +500 ppm MIT | 2-iodo-1-propenyl-phenylsulphone | 500 ppm | 0 | 1 | 2 |
| +500 ppm MIT | 3-iodomethylpyridine hydroiodide | 10 ppm | 0 | 0 | 0 |
| +500 ppm MIT | 3-bromomethylpyridine hydrobromide | 500 ppm | 0 | 0 | 1 |
| +500 ppm MIT | bromomethyl-p-phenyl-sulphone | 100 ppm | 0 | 1 | 1 |
| +500 ppm MIT | 2-bromomethyl-6-methyl-pyridine | 100 ppm | 0 | 1 | 2 |
| +500 ppm MIT | diiodomethyl-p-tolyl-sulphone | 10 ppm | 0 | 0 | 0 |
| +500 ppm MIT | N-(2-iodo-1-iodomethyl-ethyl)benzylsulphonamide | 10 ppm | 0 | 0 | 0 |
| +500 ppm MIT | folpet | 500 ppm | 0 | 1 | 1 |
| +500 ppm MIT | dichlofluanid | 500 ppm | 0 | 1 | 1 |
| +500 ppm MIT | allyl-p-tolylsulphone | 500 ppm | 0 | 1 | 1 |
| +500 ppm MIT | Tacolyn ™ 100 Resin Dispersion | 1000 ppm | 0 | 1 | 1 |
| +500 ppm MIT | Tacolyn ™ 100 Resin Dispersion | 2000 ppm | 0 | 0 | 0 |
| +500 ppm MIT | Tacolyn ™ 100 Resin Dispersion | 10.000 ppm | 0 | 0 | 0 |
| +500 ppm MIT | Tacolyn ™ 100 Resin Dispersion | 20.000 ppm | 0 | 0 | 0 |
| +500 ppm MIT | Linseed oil | 1.000 ppm | 0 | 0 | 2 |
| +500 ppm MIT | Linseed oil | 5.000 ppm | 0 | 0 | 2 |
| +500 ppm MIT | Linseed oil | 10.000 ppm | 0 | 0 | 0 |
| +500 ppm MIT | Linseed oil | 20.000 ppm | 0 | 0 | 0 |

The invention claimed is:

1. A latex paint or an emulsion paint comprising a resin, 2-methyl-4-isothiazolin-3-one and one or more inhibitors selected from the group consisting of iodoform, chlorothalonil, hydroxylamine-o-sulphonic acid, maleimide, 2,6-bisbromomethylpyridine 1-oxide, 2,6-bisdibromomethylpyridine 1-oxide, 2,6-bischloromethylpyridine, acetylacetone, diiodomethane, 2-dibromonitromethyl-3-methylpyridine, 2-iodo-1-propenyl phenyl sulphone, 3-iodomethyl-pyridine hydroiodide, gum resins, colophony resins, oil resins, linseed oil, 3-bromomethylpyridine hydrobromide, bromomethyl p-phenyl sulphone, 2-bromomethyl-6-methylpyridine, diiodomethyl p-tolyl sulphone, N-(2-iodo-1-iodomethyl-ethyl)benzylsulphonamide, N-trichloromethylthiophthalimide, dichlofluanid, allyl p-tolyl sulphone, sodium iodide, potassium iodide, bromoacetic acid, iodoacetic acid, alkyl halides, methionine, benzyl halides, dialkyl ethers, diaryl ethers, acryloalkenyl ethers, alkyl sulphonates, butylated hydroxytoluene (BHT), butylated hydroxyanisole (BHA), 2,5-di-tert-butylhydroquinone, 3,5-di-tert-butylhydroquinone, propyl gallate, ascorbic acid, isoascorbic acid, and potassium bromate wherein the latex paint or the emulsion comprises less than 0.01% by weight of 5-chloro-2-methyl-isothiazolin-3-one and the ratio of 2-methyl-4-isothiazolin-3-one to inhibitor is in the range from 1000:1 to 1:100.

2. The latex paint or an emulsion paint according to claim 1, further comprising 1,2-benzisothiazolin-3-one (BIT).

3. Method for preventing ghost odour in coating compositions, selected from the group consisting of paints, renders, polymer dispersions, wall-paints and adhesives which comprises a resin, a solvent and 2-methyl-4-isothiazolin-3-one, said method comprising adding to the coating one or more inhibitors selected from the group consisting of iodoform, chlorothalonil, hydroxylamine-o-sulphonic acid, maleimide, 2,6-bis-bromomethylpyridine 1-oxide, 2,6-bisdibromomethylpyridine 1-oxide, 2,6-bis-chloromethylpyridine, acetylacetone, diiodomethane, 2-dibromonitromethyl-3-methylpyridine, 2-iodo-1-propenyl phenyl sulphone, 3-iodomethylpyridine hydroiodide, 3-bromomethylpyridine hydrobromide, bromomethyl p-phenyl sulphone, gum resins, colophony resins, oil resins, linseed oil, 2-bromomethyl-6-methylpyridine, diiodomethyl p-tolyl sulphone, N-(2-iodo-1-iodomethylethyl)benzylsulphonamide, N-trichloromethylthiophthalixnide, dichlofluanid, allyl p-tolyl sulphone, sodium iodide, potassium iodide, bromoacetic acid, iodoacetic acid, alkyl halides, methionine, benzyl halides, dialkyl ethers, diaryl ethers, acryloalkenyl ethers, alkyl sulphonates, butylated hydroxytoluene (BHT), butylated hydroxyanisole (BHA), 2,5-di-tert-butylhydroquinone, 3,5-di-tert-butylhydroquinone, propyl gallate, ascorbic acid, isoascorbic acid, and potassium bromate wherein the coating compositions comprise 10 to 1,000 ppm 2-methyl-4-isothiazolin-3-one and one or more inhibitors in the range from 1 to 10,000 ppm.

4. A latex paint or an emulsion paint consisting of a resin, 2-methyl-4-isothiazolin-3-one and one or more inhibitors selected from the group consisting of iodoform, chlorothalonil, hydroxylamine-o-sulphonic acid, maleimide, 2,6-bis-bromomethylpyridine 1-oxide, 2,6-bisdibromomethylpyridine 1-oxide, 2,6-bischloromethylpyridine, acetylacetone, diiodomethane, 2-dibromonitromethyl-3-methylpyridine, 2-iodo-1-propenyl phenyl sulphone, 3-iodomethyl-pyridine hydroiodide, gum resins, colophony resins, oil resins, linseed oil, 3-bromomethylpyridine hydrobromide, bromomethyl p-phenyl sulphone, 2-bromomethyl-6-methylpyridine, diiodomethyl p-tolyl sulphone, N-(2-iodo-1-iodomethylethyl)benzylsulphonamide, N-trichloromethylthiophthalimide, dichlofluanid, allyl p-tolyl sulphone, sodium iodide, potassium iodide, bromoacetic acid, iodoacetic acid, alkyl halides, methionine, benzyl halides, dialkyl ethers, diaryl ethers, acryloalkenyl ethers, alkyl sulphonates, butylated hydroxytoluene (BHT), butylated hydroxyanisole (BHA), 2,5-di-tert-butylhydroquinone, 3,5-di-tert-butylhydroquinone, propyl gallate, ascorbic acid, and isoascorbic acid.

* * * * *